United States Patent

Winkowski et al.

[11] Patent Number: 6,121,197
[45] Date of Patent: Sep. 19, 2000

[54] BIOCIDAL COMPOSITION

[75] Inventors: Karen Winkowski, Highland Park, N.J.; Techen Tsao, Baton Rouge, La.

[73] Assignee: Creanova Inc., Somerset, N.J.

[21] Appl. No.: 09/317,751

[22] Filed: May 24, 1999

[51] Int. Cl.[7] .......... A01N 33/00; A01N 37/34; A01N 43/40; A01N 43/66

[52] U.S. Cl. .......... 504/155; 514/525; 514/245; 504/158

[58] Field of Search .......... 514/245, 525; 504/155, 158

[56] References Cited

U.S. PATENT DOCUMENTS

| | | | |
|---|---|---|---|
| 3,948,636 | 4/1976 | Marks | 71/112 |
| 4,260,753 | 4/1981 | Berrer et al. | 544/208 |
| 4,297,258 | 10/1981 | Long, Jr. | 260/29.6 |
| 5,125,953 | 6/1992 | Gattner et al. | 71/67 |
| 5,162,343 | 11/1992 | Whitekettle et al. | 514/345 |
| 5,328,926 | 7/1994 | Oppong | 514/372 |
| 5,401,757 | 3/1995 | Backhouse et al. | 514/347 |
| 5,585,033 | 12/1996 | Tsao et al. | 514/373 |
| 5,591,760 | 1/1997 | Hsu | 514/372 |
| 5,707,929 | 1/1998 | Kuusisto et al. | 504/155 |
| 5,716,628 | 2/1998 | Vinopal et al. | 424/405 |
| 5,716,629 | 2/1998 | Robertson et al. | 424/405 |
| 5,726,206 | 3/1998 | Oppong et al. | 514/544 |
| 5,728,730 | 3/1998 | Oppong et al. | 514/515 |
| 5,733,362 | 3/1998 | Hahn | 106/18.33 |
| 5,741,483 | 4/1998 | Okawa | 424/78.09 |
| 5,874,453 | 2/1999 | Oppong et al. | 514/367 |
| 5,877,201 | 3/1999 | Ammermann et al. | 514/417 |

FOREIGN PATENT DOCUMENTS 7900654   6/1979   WIPO .

OTHER PUBLICATIONS

Rainer Gruening, Ph.D., "IPBC Preservative Combination Systems for Material Protection", *Cosmetics and Toiletries Magazine*, vol. 112, Apr. 1997.

*Primary Examiner*—Allen J. Robinson
*Attorney, Agent, or Firm*—Abelman, Frayne & Schwab

[57] ABSTRACT

The invention is directed to a biocidal composition for inhibiting fungal and algae growth which comprises a mixture of tetrachloroisophthalonitrile and N-cyclopropyl-N'(1,1-dimethylethyl)-6-(methylthio)-1,3,5-triazine-2,4-dismine.

8 Claims, No Drawings

BIOCIDAL COMPOSITION

FIELD OF THE INVENTION

This invention is directed to a biocidal composition containing an algaecide and a fungicide and, more particularly to a biocidal composition comprising a mixture of N-cyclopropyl-N'(1,1-dimethylethyl)-6-(methylthio)-1,3,5-triazine-2,4 dismine ("CDMT") and tetrachloroisophthalonitrile ("CTL").

DESCRIPTION OF RELATED ART

CDMT is an effective algaecide for architectural paints and coatings designed to be anti-fouling. Notwithstanding that CDMT is a known algaecide, it has little or no algaecidal activity against certain algae species, i.e., unicellular blue-green algae, exemplary of which are the Cyanophyceae family, which includes such species as Oscillatoria sp., Scytonema sp., Gloeocapsa sp., Chroococcus sp., Calothrix sp., etc.

U.S. Pat. No. 5,125,953 discloses the use of CDMT in combination with other fungicides either in solution or as an aqueous dispersion in the treatment of concrete roof tiles. CDMT has an inherent disadvantage in that it has a low level of solubility in water and, thus, when it is used in the form of an aqueous dispersion for water-based coatings, it tends to settle out from a quiescent mixture. Thus, a drawback when using CDMT is that added stirring equipment and added stirring time are needed to redisperse it after settling of the solids. The '953 patent also discloses the use of CDMT with various glycols, such as ethylene glycol, diethylene glycol, propylene glycol, dipropylene glycol, etc. However, many of the ethylene glycols and their mono- and dialkyl ethers or esters are hazardous air pollutants which are not suitable for industrial applications and, further, CDMT is not sufficiently soluble in the glycols or their corresponding alkyl ethers or esters for use in industrial applications.

CTL has found extensive use as a fungicide in agricultural applications and architectural coating applications. When employed in its solid form, it is difficult to grind into a suitable coating formulation. Accordingly, it is desirable to provide CTL in a liquid formulation or coating in order to minimize and reduce the hazardous handling conditions and difficulties associated with grinding it into a coating formulation.

U.S. Pat. No. 3,948,636 discloses the formulation of CTL as a flowable aqueous dispersion. WO 79/00654 discloses the use of CTL in surfactants in non-aqueous media for use in coating applications. U.S. Pat. No. 5,401,757 discloses the use of CTL in biocidal compositions with substituted urea and sulphoxide or sulphone.

Notwithstanding the fact that CTL has been promoted and used extensively as a fungicide, it has also been found to be effective as an algaecide against unicellular blue-green algae from the Cyanophyceae family, which includes species such as Oscillatoria sp., Scytonema sp., Gloeocapsa sp., Chroococcus sp., Calothrix sp., etc. These algae species are commonly found on substrates to be covered with exterior paints, in sea water environments and on various coatings.

SUMMARY OF THE INVENTION

It has now been found that a composition comprising a mixture of CDMT and CTL provides a broader spectrum of activity against fungi and algae than either of the components when used individually. The combination of the two also permits the use of lesser quantities of CDMT and CTL to obtain comparable or better fungal and algae inhibition than when they are used individually. The biocidal mixture of the present invention provides a formulation which is environmentally friendly and easy to use in many coating applications.

DETAILED DESCRIPTION OF THE INVENTION

The present invention is directed to a mixture of two biocides suitable for controlling unwanted fungicidal and algaecidal growth in water-based and solvent-based applications. The liquid biocidal compositions of the present invention comprise a mixture of CDMT and CTL. The weight % of CDMT in the composition of the present invention ranges from about 0.2% to about 50%, more preferably from about 2% to about 20% and most preferably from about 5% to about 10%. The weight % of CTL in the composition of the present invention ranges from about 5% to about 60%, more preferably from about 20% to about 50% and most preferably from about 40% to about 50%.

The weight ratio of CTL to CDMT in the composition is from about 1:10 to about 45:1, with a preferred weight ratio of about 10:1.

The composition also contains from about 0.2% to about 10% by weight of surfactants, preferably from about 4% to about 8%, by weight. The surfactants function as wetting agents, emulsifiers, dispersing agents and defoaming agents for both CDMT and CTL. Suitable surfactants are EO/PO block copolymers, such as Witcomol®324, sulfo succinates, naphthalene sulfonates and acrylic graft copolymers.

The composition can also contain from about 0% to about 10%, by weight, preferably from about 2% to about 7%, by weight, of an organic solvent which is environmentally friendly for the purpose of functioning as a co-solvent in order to stabilize the composition of this invention in the form of its aqueous dispersion. Exemplary of the solvents which can be employed are propylene glycol methyl ether, dipropylene glycol methyl ether, tripropylene glycol methyl ether, and other common solvents which are known for use in coating applications.

The composition also can contain from about 0% to about 5% of fused silica, modified or unmodified carbohydrate polymer, a polyurethane polymer or an acrylic polymer which functions as a thickener or anti-settling agent for the mixture by means of which the viscosity is established and maintained over time and also to prevent the settling of solids with the passage of time.

The composition of the present invention has utility for retarding microbial growth including fungal and algae growth in paints, marine anti-fouling coatings, cooling towers, metal working fluids, fuel systems, swimming pools, coatings, fabric, leather, paper, wood, cosmetic formulations and other personal care products, fuel systems, therapeutic pharmaceutical formulations, and the like.

The examples presented below serve to illustrate the invention and to demonstrate the broad spectrum of activity of the composition of the present invention for the inhibition of fungal and algae growth.

The biocidal activity of CTL and CDMT was determined by testing a range of concentrations and ratios of CTL and CDMT on polyvinyl acrylic paint. The microbiological evaluations shown as examples are based on ASTM D 5590-94 (Determining the resistance of paint films and related coatings to fungal defacement by accelerated four-week agar plate assays) and ASTM D5589-94 (Standard test method for determining the resistance of paint films and related coatings to algae defacement).

Paint samples were prepared to contain different concentrations of each biocide or their mixtures in different concentrations and ratios. Each paint thus prepared was then brush coated onto strips of drawdown paperboard. The strips were air-dried for 24 hours. Each strip was then cut into 1 ⅛ inch squares, steam sterilized and placed on the surface of solidified agar.

A. Fungal evaluations were performed on Malt agar from Sigma Chemical. The fungi *Aspergillus niger* ATCC 6275 and *Penicilium funiculosum* ATCC 11797 were grown on malt agar for 10 days and a spore suspension was prepared by washing the spores from the plate into a sterile water solution. Equal amounts of each spore suspension were mixed. The final mixed spore suspensions contain approximately $10^6$ spores/ml. One ml. of the mixed spore suspension was added to the paint strip on Malt agar. Inoculated plates were incubated at 28° C. under 85–90% relative humidity for four weeks.

B. Algae evaluations were performed on Allen's agar plates. To prepare the medium, the following ingredients were added to 1.0 liter of deionized water: 1.5 g of $NaNO_3$, 0.039 g of $K_2HPO_4$, 0.075 g of $MgSO_4 \cdot 7H_2O$, 0.027 g of $CaCl_2 \cdot 2H_2O$, 0.02 g of $Na_2CO_3$, 0.058 g of $Na_2SiO_3 \cdot 9H_2O$, 0.006 g of Ferric Citrate (autoclaved and added separately after cooling), 0.006 g of citric acid, 0.001 g of EDTA and 1.0 ml of Allen's trace-element. The trace-element solution was prepared by adding to 1.0 liter of deionized water, 2.86 g of $H_3BO_3$, 1.81 g of $MnCl_2 \cdot 4H_2O$, 0.222 g of $ZnSO_4 \cdot 7H_2O$, 0.391 g of $Na_2MoO_4 \cdot 2H_2O$, 0.079 g of $CuSO_4 \cdot 5H_2O$ and 0.0494 g of $Co(NO_3)_2 \cdot H_2O$. The pH of the medium was adjusted to 7.8 with 1 N NaOH. For solid media, 1.5% of bacto agar (sigma) was added. Each algae (Chlorella sp. ATCC 7516, *Scenedesums quadricauda* ATCC 11460, *Ulothrix gigas* ATCC 30443, Calothirx sp. ATCC 27914 or Gloeocapsa sp. ATCC 29115) was grown on 3N Bold's Basal Medium for 10 days and the cell suspension prepared by washing the cells from the plate into a sterile water solution. Equal amounts of each algae suspension were mixed. The final algae suspension contained approximately $10^6$ cells/ml. One ml. of the mixed algae suspension was added to the paint strip on Allen's agar. The inoculated plates were then incubated at 25° C. for 10–15 days under a light-dark cycle of 14–10 hours.

Growth inhibition on the painted square was recorded based on a scale of "0" to "10" where "0" corresponds to 100% inhibition and "10" corresponds to 0% growth inhibition. The test results demonstrating overlapping activities are shown in Table 1.

TABLE 1

| | Fungi | | | Algae | | |
|---|---|---|---|---|---|---|
| Compound | PPM (added to paint) | Rating | % inhibition | PPM (added to paint) | Rating | % inhibition |
| CTL | 400 | 0 | 100 | 400 | 2 | 80 |
| CDMT | 150 | 9 | 10 | 45 | 0 | 100 |
| CTL:CDMT | 240:30 | 0 | 100 | 320:7.5 | 0 | 100 |

CTL is most effective as a fungicide and CDMT as an algaecide. The combination of both active compounds, however, unexpectedly broadens the spectrum of fungicidal and algaecidal activity.

Table 1 also demonstrates that the present invention permits the use of lesser amounts of CTL and CDMT when used in a mixture, while obtaining comparable or better results. For example, a comparable level of fungal inhibition was obtained when a significantly smaller quantity of CTL was used in combination with CDMT than when it was used individually, while simultaneously providing 100% algae inhibition. In a similar vein, when CDMT was combined with CTL, the quantity of CDMT needed to obtain 100% algae inhibition was ⅙ th the quantity needed when CDMT was used individually, while simultaneously providing 100% fungal inhibition.

What is claimed is:

1. A composition for controlling fungal and algae growth which comprises a synergistically fungicidally and algaecidally effective amount of a mixture of tetrachloroisophthalonitrile (CTL) and N-cyclopropyl-N'(1,1-dimethylethyl)-6-(methylthio)-1,3,5-triazine-2,4-dismine (CDMT).

2. The composition of claim 1 wherein the CTL is from about 5.0% to about 60.0%, by weight, and the CDMT is from about 0.2% to about 50%, by weight, of the composition.

3. The composition of claim 1 wherein the weight ratio of CTL to CDMT is from about 1:10 to about 45:1.

4. The composition of claim 3 wherein the weight ratio of CTL to CDMT is about 10:1.

5. A method of controlling the growth of fungi and algae in an aqueous formulation which comprises adding to said aqueous formulation a synergistically fungicidally and algaecidally effective amount of a mixture of tetrachloroisolphthalonitrile (CTL) and N-cyclopropyl-N'(1,1-dimethylethyl)-6-(methylthio)-1,3,5-triazine-2,4-disimine (CDMT).

6. The method of claim 5 wherein the CTL is from 5.0% to about 60.0%, by weight, and the CDMT is from about 0.2% to about 50%, by weight, of the composition.

7. The method of claim 5 wherein the weight ratio of CTL to CDMT is from about 1:10 to about 45:1.

8. The method of claim 7 wherein the weight ratio of CTL to CDMT is about 10:1.

* * * * *